United States Patent
Ikegami et al.

(10) Patent No.: US 7,397,382 B2
(45) Date of Patent: Jul. 8, 2008

(54) DROWSINESS DETECTING APPARATUS AND METHOD

(75) Inventors: Tatsuya Ikegami, Nisshin (JP); Shinji Nanba, Kariya (JP); Kenichi Yanai, Nisshin (JP)

(73) Assignee: DENSO CORPORATION, Kariya (JP)

(*) Notice: Subject to any disclaimer, the term of this patent is extended or adjusted under 35 U.S.C. 154(b) by 404 days.

(21) Appl. No.: 11/159,147

(22) Filed: Jun. 23, 2005

(65) Prior Publication Data

US 2006/0038689 A1 Feb. 23, 2006

(30) Foreign Application Priority Data

Aug. 23, 2004 (JP) ............... 2004-242386

(51) Int. Cl.
*G08B 23/00* (2006.01)
(52) U.S. Cl. .................. 340/575; 340/576; 701/1
(58) Field of Classification Search ......... 340/575, 340/576, 438, 573.1; 600/300; 701/1
See application file for complete search history.

(56) References Cited

U.S. PATENT DOCUMENTS

| | | | | |
|---|---|---|---|---|
| 4,611,199 A | * | 9/1986 | Seko et al. ............. | 340/576 |
| 4,706,072 A | * | 11/1987 | Ikeyama ............... | 340/576 |
| 6,669,632 B2 | | 12/2003 | Nanba et al. ........... | 600/300 |
| 7,266,430 B2 | * | 9/2007 | Basson et al. .......... | 701/1 |
| 2004/0193068 A1 | * | 9/2004 | Burton et al. .......... | 600/544 |
| 2006/0044144 A1 | * | 3/2006 | Duval .................... | 340/576 |

FOREIGN PATENT DOCUMENTS

JP   A-H07-232571   9/1995

* cited by examiner

*Primary Examiner*—Phung T. Nguyen
(74) *Attorney, Agent, or Firm*—Posz Law Group, PLC

(57) ABSTRACT

A drowsiness detecting apparatus has a pulse wave sensor and a determination circuit. The sensor is provided to a steering wheel to detect a pulse wave of a vehicle driver gripping the steering wheel. The determination circuit generates a thorax pressure signal indicative of the depth of breathing by envelope-detecting a pulse wave signal of the sensor and determines whether the driver is drowsy by comparing a pattern of the thorax pressure signal with a reference pattern. The display and the buzzer notify the driver and any other passengers in the vehicle of the drowsiness of the driver by a visual indication and buzzing sound, respectively. A body surface motion may be used as a signal that indicates the depth of breathing.

18 Claims, 4 Drawing Sheets

DROWSINESS DETECTING APPARATUS AND METHOD

CROSS REFERENCE TO RELATED APPLICATION

This application is based on and incorporates herein by reference Japanese patent application No. 2004-242386 filed on Aug. 23, 2005.

FIELD OF THE INVENTION

The present invention relates to automatic drowsiness detecting apparatus and method for automatically detecting drowsiness of a person such as a vehicle driver.

BACKGROUND OF THE INVENTION

Various drowsy driving preventing apparatuses are proposed. In one apparatus proposed in JP 7-232571A, for instance, the apparatus detects drowsiness or sleepiness of a vehicle driver based on behavior of the driver while driving a vehicle, and cautions the driver for a safety driving.

Specifically, a wheel gripping pressure applied to a steering wheel of a vehicle by a vehicle driver and a position of application of such a wheel gripping pressure are detected. A seating pressure applied to a driver seat of the vehicle by the driver and a position of exertion of such a seating pressure are detected. Some flavor is provided to stimulate the driver, when the position of application of the wheel gripping pressure changes to or more times per hour. Air pressure of the driver seat is varied to stimulate the driver, when the seating pressure changes 50% or more and the position of application of the seating pressure changes two or more times per hour. A buzzing sound is provided to stimulate the driver, when the wheel gripping pressure changes 50% or more from a normal condition.

In the above apparatus, the wheel gripping pressure cannot be detected, if the driver fails to grip the steering wheel for some reason. Further, the seating pressure largely varies from person to person. It is therefore difficult to accurately detect the drowsiness of sleepiness of a driver.

As an alternative method for detecting drowsiness of a driver, it is proposed to use biometric information such as a heart rate or a pulse rate to detect the drowsiness. It is however become necessary to have a comparison reference data about degree of drowsiness. This reference data must be pre-stored as a heart rate or a pulse rate in the awakened condition of a driver. Alternatively the reference data must be set by sampling the heart rate or the pulse rate immediately after the driver gets in the vehicle.

Pre-storing of the reference data requires the identification of each driver so that the reference data may be set for the specific driver. Sampling of the heart rate or the pulse rate for setting the reference data requires some time. Further the sampling should be started only after the heart rate and the pulse rate become stable, because the heart rate and the pulse rate varies with the behavior of the driver before getting in the vehicle.

SUMMARY OF THE INVENTION

It is therefore an object of the present invention to provide drowsiness detecting apparatus and method, which do not use a reference data specific to each person, instantly start drowsiness determination operation and detect drowsiness with high accuracy.

According to the present invention, a depth of breathing of a person is detected, and drowsiness of the person is determined when the depth of breathing falls in a predetermined breathing condition including at least one of a sudden decrease in the depth of breathing and a periodic repetition of deep breathing and shallow breathing.

Preferably, the periodic repetition is set to 3 to 7 breaths. The depth of breathing is detected based on a thorax pressure of the person, which is generated by detecting a pulse wave of the person and processing a pulse wave signal. Alternatively, the depth of breathing is detected based on a body surface motion of the person.

To use the drowsiness detection for a vehicle driver, the pulse wave is detected by a pulse wave sensor attached to a steering wheel of the vehicle to be gripped by the driver. The body surface motion is detected by a pressure sensor attached to at least one of a bottom surface, a back surface and a side surface of a seat.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

Figure 1:
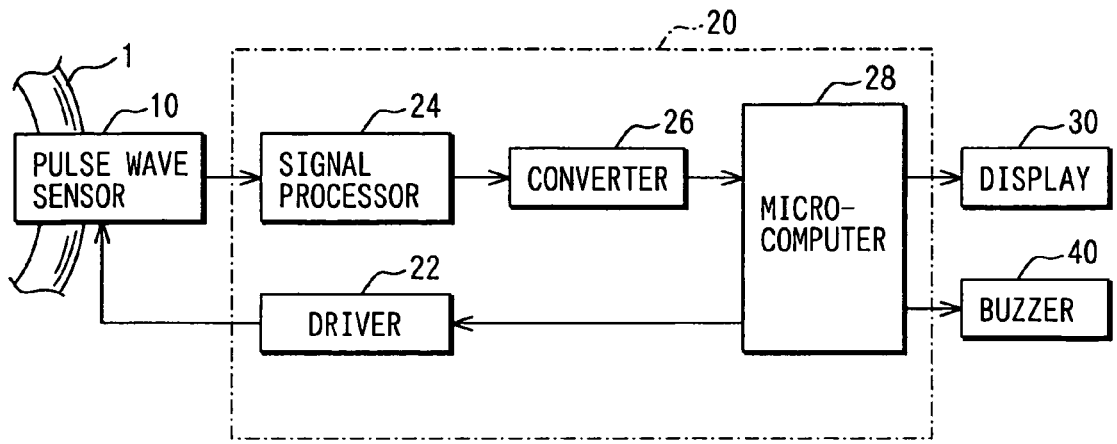
FIG. 1 is a block diagram showing a drowsiness detecting apparatus according to an embodiment of the present invention.

A drowsiness detecting apparatus according to an embodiment is applied to a vehicle to detect drowsiness of a vehicle driver for a safety driving. As shown in FIG. 1, the apparatus has a pulse wave sensor 10, a determination circuit 20, a display 30 and a buzzer 40. The sensor 10 is installed in a vehicle steering wheel 1 to detect a pulse wave of a vehicle driver gripping the steering wheel 1. The determination circuit 20 is connected to the sensor 10 to determine whether the driver is drowsy based on the pulse wave detected by the sensor 10. The display 30 and the buzzer 40 are connected to the determination circuit 20 to inform the driver and any other passengers in the vehicle of the drowsiness of the driver by a visual indication and buzzing sound, respectively.

The sensor 10 may be an optical reflection-type sensor, which has a light emitting element and a light receiving element to detect the pulse wave of the driver. The light emitting element emits light to a wheel gripping hand of the driver and receives reflected light by the light receiving element.

The determination circuit 20 includes a driver 22, a signal processor 24, and A/D converter 26 and a microcomputer 28. The driver 22 activates and drives the sensor 10 under control of the microcomputer 28. The signal processor 24 processes a pulse wave signal produced from the sensor 10 and generate an analog thorax pressure signal indicative of a pressure inside the thorax of the driver. This pressure varies with the depth of breath of the driver. The A/D converter 26 converts the thorax pressure signal to a digital signal. The microcomputer 28 receives the digital signal of the thorax pressure and determines the drowsiness of the driver based on changes in the thorax pressure. The display 30 and the buzzer 40 are activated when the drowsiness is determined.

Figure 2:
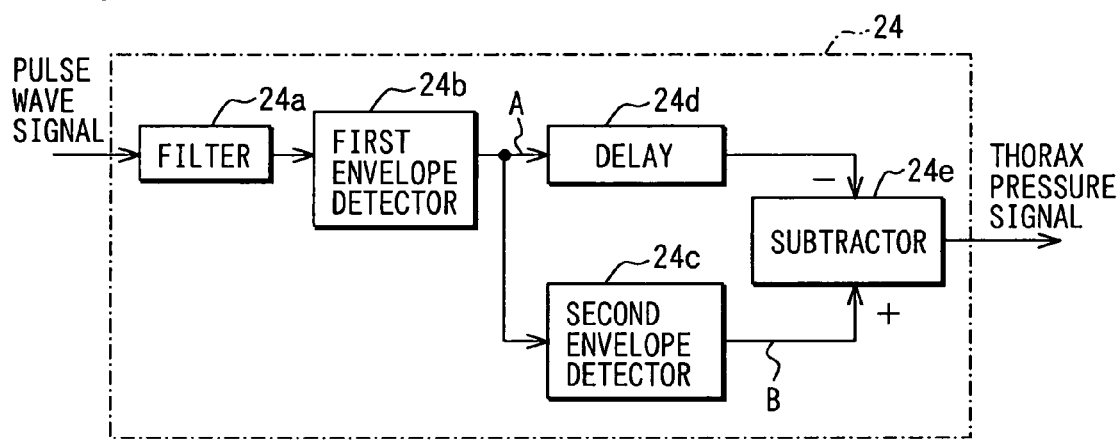
FIG. 2 is a circuit diagram showing a signal processor used in the embodiment.
Figure 4:
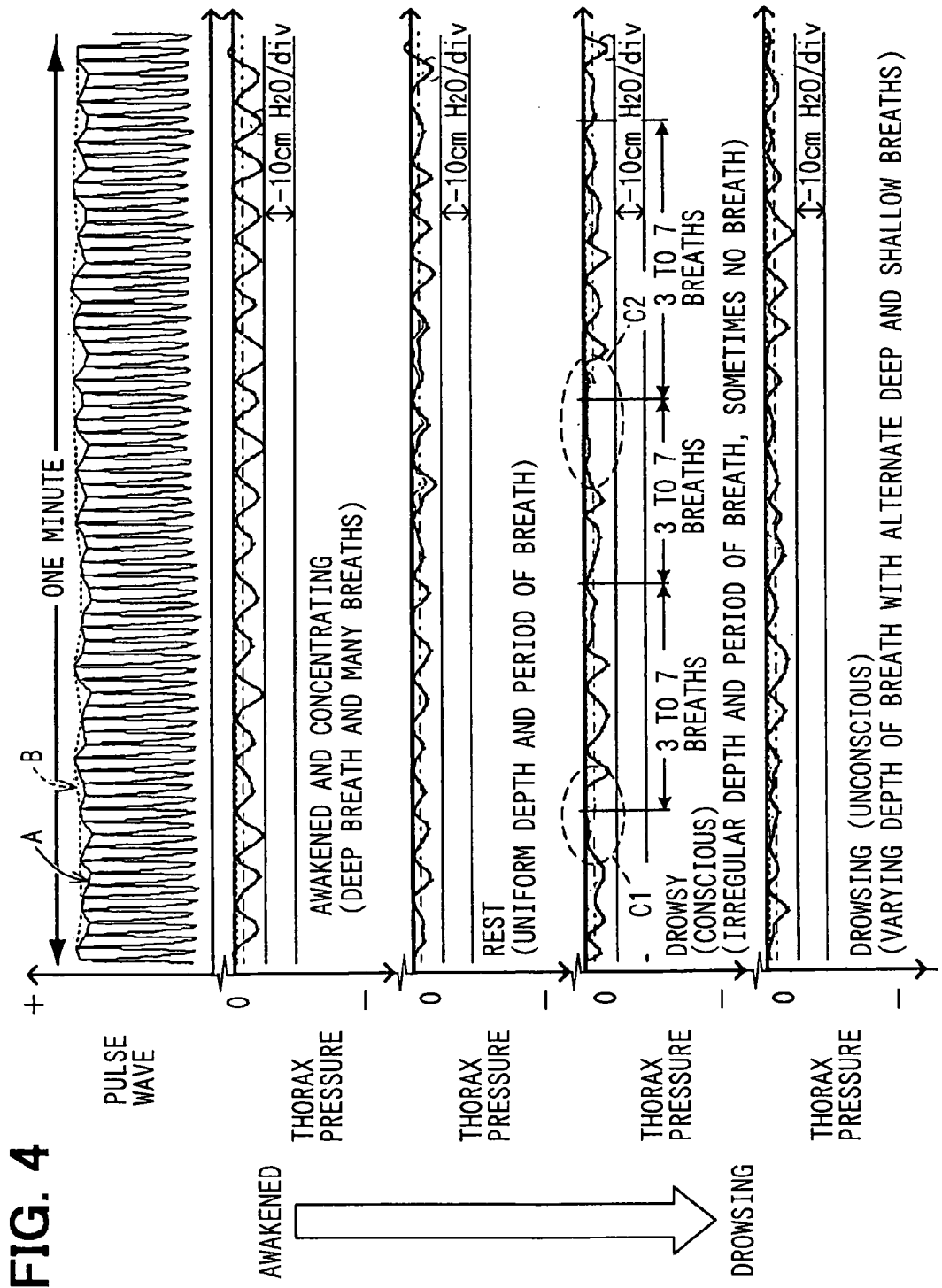
FIG. 4 is a chart showing correlation between changes of a pulse wave and a thorax pressure in the case of transition of a person from an awakened condition to a drowsing condition.

The thorax pressure may be detected from the pulse wave in the conventional manner, e.g., U.S. Pat. No. 6,669,632 (JP 2002-355227A). For this purpose, the signal processor 24 for generating the thorax pressure signal may be constructed as shown in FIG. 2. Specifically, it includes a band pass filter 24a, a first envelope detector 24b, a second envelope detector 24c, a delay 24d and a subtractor 24e. The filter 24 filters out unnecessary signal components from the pulse wave signal applied from the senor 10. The unnecessary signal components are specifically external disturbance light noises of more than 3 Hz and signals of less than 0.1 Hz corresponding to body motion of the driver. The first envelope detector 24b detects an envelope of the pulse wave signal applied from the filter 24a and generates a breathing signal A as shown in FIG. 4. The second envelope detector 24c detects an envelope of the breathing signal A to generate an output signal B as shown in FIG. 4. The delay 24 delays the breathing signal A to synchronize the breathing signal A and the output signal B in phase. The subtractor 24e subtracts the breathing signal A delayed by the delay 24d from the output signal B to generate the thorax pressure signal.

The microcomputer 28 is known well and includes a CPU, a ROM, a RAM and others. In the microcomputer 28, the CPU executes drowsiness detecting processing shown in FIG. 5 based on a program pre-stored in the ROM. The drowsiness detecting processing is repeated after a battery power is supplied to the determination circuit 20 through an ignition switch (not shown) and the microcomputer 28 is activated.

The following drowsiness detecting processing is based on the finding that, as understood from FIG. 4, the thorax pressure generally changes in a fixed manner when a person condition changes from awakened to drowsing and does not largely change unlike the heart rate or pulse rate which is very dependent on the motion of a person. That is, the change in the thorax pressure indicative of the depth of breathing does not vary so much among different persons.

When the person starts to feel drowsy from the awakened condition or from the rest condition, the depth and period of breathing does not remain stable and the breathing sometimes cannot be found. In this instance, the depth of the breathing suddenly becomes shallow or alternately becomes deep and shallow in three to seven breaths. When the person fall asleep, the breathing is repeated periodically although the depth of breathing slightly changes.

In this processing, the sensor 10 is first activated by the driver 22 at step 100. Then, at step 110, a time measurement is started by resetting and subsequently operating an internal timer. At step 120, the thorax pressure detected by the signal processor 24 and indicated by the digital signal of the A/D converter 26 is sampled. At step 130, it is determined whether it is a time to determine the drowsiness. Specifically, it is determined whether the time measured by the internal timer from the sampling reaches a predetermined period. If it is not the time, the processing returns to step 120. Thus, in steps 110 to 130, the thorax pressure is sampled repeatedly during the predetermined period to generate a time-sequential pressure pattern (data) indicative of signal waveform of the thorax pressure.

Figure 3:
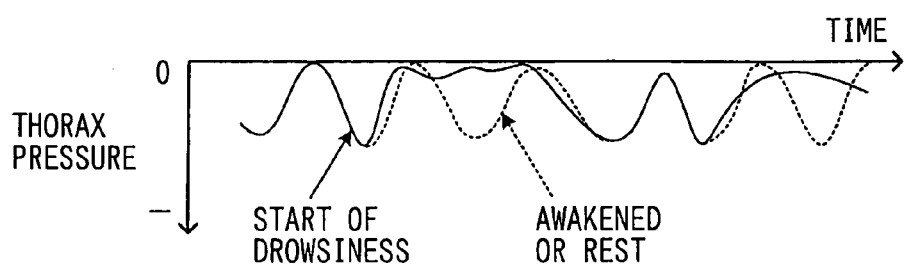
FIG. 3 is a chart showing changes of a thorax pressure in a drowsing condition and an awakened rest condition.

If it is the time, a reference pattern (data) for comparison is read from the ROM at step 140. This reference pattern may be predetermined by standardizing changes in thorax pressure which generally occur when a person becomes drowsy. It is noted that, as shown in FIG. 3, the patterns of thorax pressure changes between the drowsy condition (solid line) and the awakened or rest condition (dotted line). The thorax pressure tends to remain unchanged when the driver starts to feel drowsy. Therefore, for instance, the changes in areas C1, C2 and the like in FIG. 4 may be standardized. At step 150, the time-sequential pressure pattern is compared with the reference pattern to calculate a degree of agreement (correlation) between the two patterns. This comparison may be made by using a known pattern matching technique.

Then at step 160, the calculated correlation is compared with a predetermined reference. If the calculated correlation is larger than the reference, it is determined that the driver feels drowsy. In this instance, at step 170, the display 30 and the buzzer 40 are activated to notify and caution the driver and the other passengers in the vehicle. If the calculated correlation is not large enough, the processing returns to step 110.

After step 170, it is checked at step 180 whether the driver or other passenger has input a detection stop input by an operation switch (not shown) which may be provided on the display 30. The sensor 10 is deactivated at step 190 to stop the drowsiness detecting processing, if the stop input is made. If no stop input is made, the processing returns to step 110 to repeat the same processing.

The above embodiment may be modified in various ways.

For instance, it is possible to detect the drowsiness by comparing the sampled thorax pressure pattern and a plurality of reference patterns and calculating degrees of agreement (correlations) therebetween. The plurality of reference patterns may be patterns of periodic changes of the thorax pressure in each of an awakened condition, a rest condition, a drowsing condition, etc. of a person other than the drowsy condition. The drowsiness may be determined if the calculated correlations are less than a predetermined value, that is, little correlation.

It is also possible to detect the drowsiness by calculating a difference between two adjacent negative peak values (local minima) in the thorax pressure wave shown in FIG. 4 and comparing the difference with a predetermine value. If the difference is large, it indicates that the person feels drowsiness.

It is further possible to detect the drowsiness by sequentially integrating the thorax pressures between two adjacent zero-cross points (local maximals) and calculating a difference between the two adjacent integrated values. If the difference is large, it indicates that the person feels drowsiness.

Figure 5:
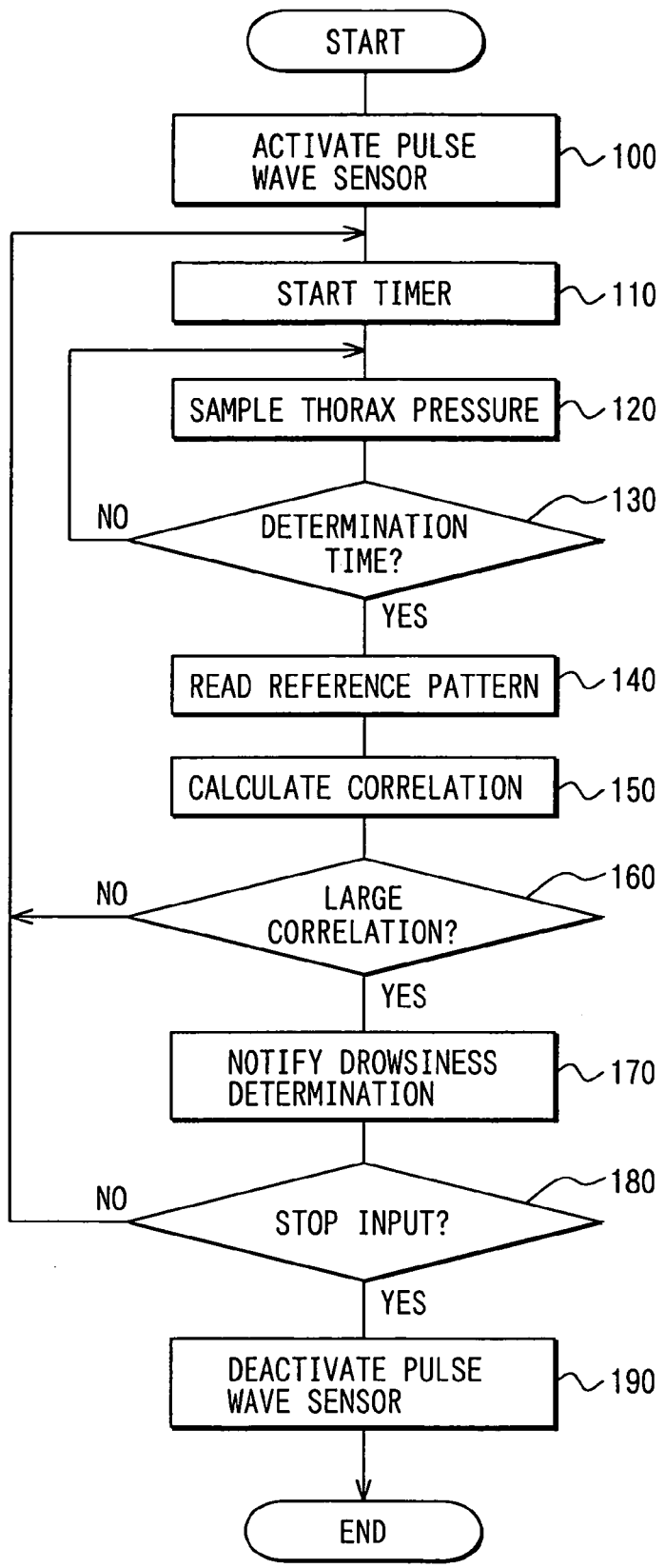
FIG. 5 is a flow chart showing drowsiness determination processing executed in the embodiment.
Figure 6:
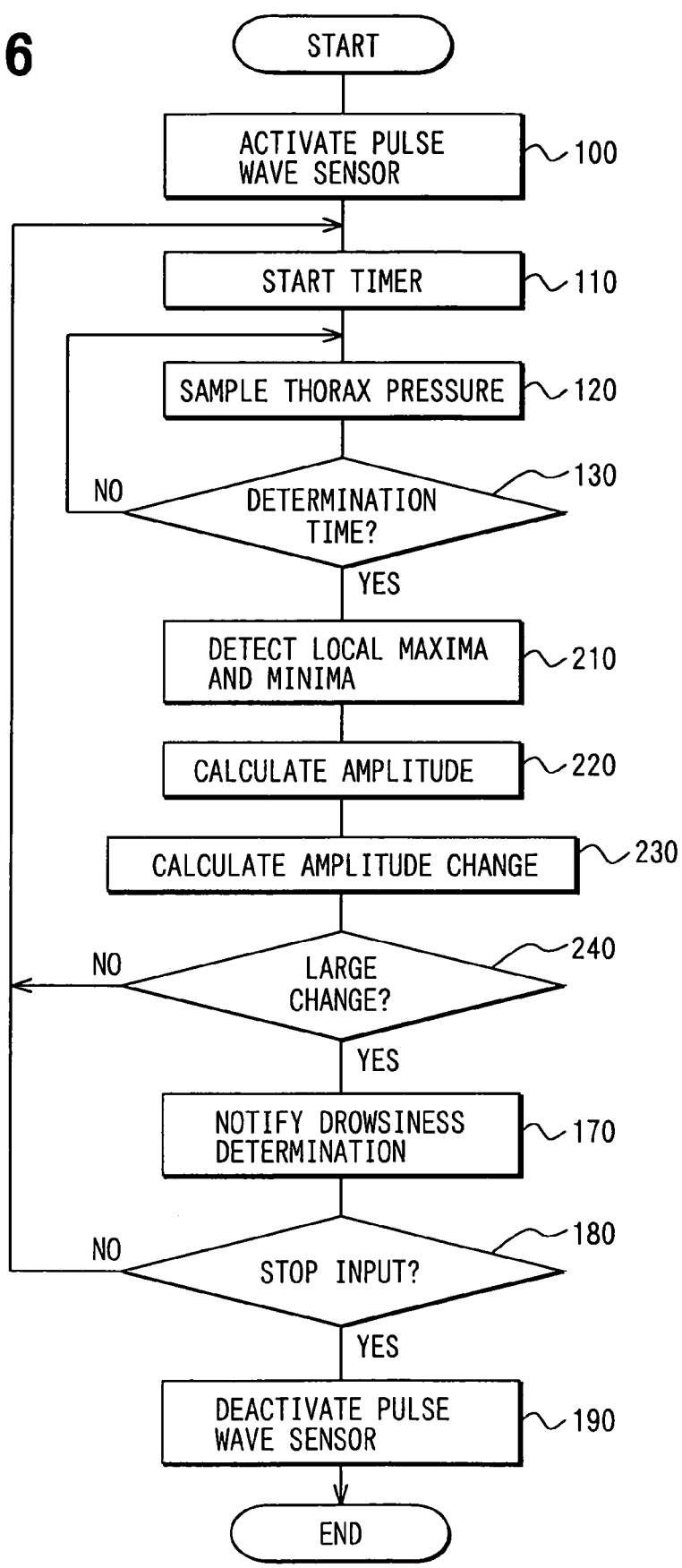
FIG. 6 is a flow chart showing a modification of the drowsiness determination processing shown in FIG. 5.

In addition, the drowsiness determining processing may be executed as shown in FIG. 6. In this processing, steps 140 to 160 in FIG. 5 are replaced with steps 210 to 240. Specifically, following steps 110 to 130 for sampling the thorax pressure, local maxima and local minima of the sampled thorax pressure are detected time-sequentially at step 210. From the local maxima and the local minima, the difference between the local maxima and the local minima is calculated as an amplitude time-sequentially at step 220. Then at step 230, a change between successive amplitudes is calculated time-sequentially. This calculated change is compared with a predetermined value at step 240. If the change is large, the drowsiness is determined and notified at step 170. If the change is small, no drowsiness is determined.

The signal processor 24 for generating the thorax pressure signal from the pulse wave signal may be constructed as a digital unit using a digital filter by eliminating the A/D converter 26. Alternatively, the thorax pressure data may be provided digitally in the microcomputer 28 from the pulse wave signal from the sensor 10. In this instance, a peak value of each local maxima (or local minima) may be detected and connected to be an envelope of a breathing signal, and a peak value of each local maxima (or local minima) of the breathing signal is detected and connected to be an other envelope.

The depth of breathing of a person may be detected from a body surface movement of a driver in place of the thorax pressure. In this case, the sensor 10 in FIG. 1 may be constructed as a body surface motion sensor such as a pressure sensor and may be provided on at least one of a bottom surface, a back surface and a side surface of a vehicle to be responsive to motions of the driver. A signal indicative of the depth of breathing may be generated by processing an output signal of the sensor and used for detecting the drowsiness in place of the thorax pressure signal. It is noted that the detection signal of the sensor must be filtered to extract a signal varying with breathing, because the body surface motion of the person is caused not only by the breathing but also intentionally.

The drowsiness may be determined by analyzing the thorax pressure by the use of chaos analysis technique, wavelet analysis technique and the like.

The drowsiness detection may be applied to not only vehicle drivers but also any other persons such as students, workers and the like.

What is claimed is:

1. A drowsiness detecting apparatus comprising:
   breath depth detecting means for detecting a depth of breathing of a person; and
   determining means for determining drowsiness of the person, when the depth of breathing falls in a predetermined breathing condition including at least one of a sudden decrease in the depth of breathing and a periodic repetition of deep breathing and shallow breathing,
   wherein the periodic repetition is set to 3 to 7 breaths.

2. The drowsiness detecting apparatus as in claim 1, further comprising:
   notifying means for notifying drowsiness of the person when the drowsiness is determined by the determining means.

3. A drowsiness detecting apparatus comprising:
   breath death detecting means for detecting a depth of breathing of a person; and
   determining means for determining drowsiness of the person, when the depth of breathing falls in a predetermined breathing condition including at least one of a sudden decrease in the depth of breathing and a periodic repetition of deep breathing and shallow breathing,
   wherein the breath depth detecting means includes:
   a pulse wave sensor provided to a vehicle steering wheel for detecting a pulse wave of the person; and
   a signal processor for detecting the depth of breathing based on a thorax pressure inside a thorax of the person by processing a pulse wave signal produced by the pulse wave sensor to detect the thorax pressure.

4. A drowsiness detecting apparatus comprising:
   breath depth detecting means for detecting a depth of breathing of a person; and
   determining means for determining drowsiness of the person, when the depth of breathing falls in a predetermined breathing condition including at least one of a sudden decrease in the depth of breathing and a periodic repetition of deep breathing and shallow breathing,
   wherein the breath depth detecting means includes:
   a body surface motion sensor provided to a vehicle seat for detecting a motion of a body surface of the person; and
   a signal processor for detecting the depth of breathing by processing a detection signal produced by the body surface motion sensor.

5. A drowsiness detecting apparatus comprising:
   breath depth detecting means for detecting a death of breathing of a person; and
   determining means for determining drowsiness of the person, when the depth of breathing falls in a predetermined breathing condition including at least one of a sudden decrease in the depth of breathing and a periodic repetition of deep breathing and shallow breathing,
   wherein the determining means samples the depth of breathing for a predetermined period to generate a breathing waveform and compares the breathing waveform with a predetermined reference pattern.

6. A drowsiness detecting apparatus comprising:
   breath depth detecting means for detecting a depth of breathing of a person; and
   determining means for determining drowsiness of the person, when the death of breathing falls in a predetermined breathing condition including at least one of a sudden decrease in the depth of breathing and a periodic repetition of deep breathing and shallow breathing,
   wherein the determining means samples the depth of breathing for a predetermined period to generate a breathing waveform, calculates a change in amplitude of the breathing waveform and compares the change in amplitude with a predetermined reference value.

7. A drowsiness detecting apparatus comprising:
   breath depth detecting means for detecting a depth of breathing of a person; and
   determining means for determining drowsiness of the person, when the depth of breathing falls in a predetermined breathing condition including at least one of a sudden decrease in the depth of breathing and a periodic repetition of deep breathing and shallow breathing,
   wherein the breath depth detecting means is thorax pressure detecting means that detects a thorax pressure inside a thorax of the person as the breath depth.

8. The drowsiness detecting apparatus as in claim 7, wherein the periodic repetition is set to 3 to 7 breaths.

9. The drowsiness detecting apparatus as in claim 7, wherein the thorax pressure detecting means includes:
   a pulse wave sensor provided to a vehicle steering wheel for detecting a pulse wave of the person; and
   a signal processor for detecting the thorax pressure by processing a pulse wave signal of the pulse wave sensor to detect the thorax pressure.

10. The drowsiness detecting apparatus as in claim 7, wherein the determining means samples the thorax pressure for a predetermined period to generate a thorax pressure waveform and compares the thorax pressure waveform with a predetermined reference pattern.

11. The drowsiness detecting apparatus as in claim 7, wherein the determining means samples the thorax pressure for a predetermined period to generate a thorax pressure waveform, calculates a change in amplitude of the thorax pressure waveform and compares the change in amplitude with a predetermined reference value.

12. A drowsiness detecting method comprising:
    detecting a depth of breathing of a person; and
    determining drowsiness of the person, when the depth of breathing falls in a predetermined breathing condition including at least one of a sudden decrease in the depth of breathing and a periodic repetition of deep breathing and shallow breathing, wherein the periodic repetition is set to 3 to 7 breaths.

13. The drowsiness detecting method as in claim 12, further comprising:

notifying drowsiness of the person when the drowsiness is determined.

14. A drowsiness detecting method comprising:

detecting a depth of breathing of a person; and determining drowsiness of the person, when the depth of breathing falls in a predetermined breathing condition including at least one of a sudden decrease in the depth of breathing and a periodic repetition of deep breathing and shallow breathing, wherein the detecting includes:

detecting a pulse wave of the person by a pulse wave sensor; and detecting the depth of breathing based on a thorax pressure inside a thorax of the person by processing a pulse wave signal produced by the pulse wave sensor to detect the thorax pressure.

15. A drowsiness detecting method comprising:

detecting a depth of breathing of a person; and determining drowsiness of the person, when the depth of breathing falls in a predetermined breathing condition including at least one of a sudden decrease in the depth of breathing and a periodic repetition of deep breathing and shallow breathing, wherein the detecting includes:

detecting a motion of a body surface of the person by a body surface motion sensor provided to a vehicle seat; and detecting the depth of breathing by processing a detection signal produced by the body surface motion sensor.

16. A drowsiness detecting method comprising:

detecting a depth of breathing of a person; and determining drowsiness of the person, when the depth of breathing falls in a predetermined breathing condition including at least one of a sudden decrease in the depth of breathing and a periodic repetition of deep breathing and shallow breathing, wherein the detecting includes sampling the depth of breathing for a predetermined period to generate a breathing waveform, and determining includes comparing the breathing waveform with a predetermined reference pattern.

17. A drowsiness detecting method comprising:

detecting a depth of breathing of a person; and determining drowsiness of the person, when the depth of breathing falls in a predetermined breathing condition including at least one of a sudden decrease in the depth of breathing and a periodic repetition of deep breathing and shallow breathing, wherein the determining includes sampling the depth of breathing for a predetermined period to generate a breathing waveform, calculating a change in amplitude of the breathing waveform and comparing the change in amplitude with a predetermined reference value.

18. The drowsiness detecting method as in claim 17, wherein the breathing waveform is generated by detecting each local maxima and local minima of sampled depth of breathing.

* * * * *